United States Patent
Cho et al.

(10) Patent No.: US 10,918,330 B2
(45) Date of Patent: Feb. 16, 2021

(54) DIABETES MANAGEMENT METHOD AND SYSTEM FOR SAME

(71) Applicants: HEALTHCONNECT CO., LTD., Seoul (KR); INVITES HEALTHCARE CO., LTD, Seoul (KR)

(72) Inventors: Young Min Cho, Seoul (KR); Soo Heon Kwak, Seoul (KR); Eun Ky Kim, Seoul (KR); Seoung Su Baek, Seoul (KR); Seung Lyeol Lee, Seoul (KR); Jin Beom Choi, Seoul (KR); Mi Young Kim, Seongnam-si (KR); Seok Won Jang, Seoul (KR); Jung Hoon Lee, Seoul (KR); Hye Kyung Hwang, Goyang-si (KR); Sue Jin Lee, Seoul (KR); Hyo Jung Kim, Seoul (KR); Su Jin Park, Yongin-si (KR); Jin Hee Do, Goyang-si (KR)

(73) Assignees: HEALTHCONNECT CO., LTD., Seoul (KR); INVITES HEALTHCARE CO., LTD., Seoul (KR)

( * ) Notice: Subject to any disclaimer, the term of this patent is extended or adjusted under 35 U.S.C. 154(b) by 188 days.

(21) Appl. No.: 16/087,495

(22) PCT Filed: Mar. 22, 2016

(86) PCT No.: PCT/KR2016/002846
§ 371 (c)(1),
(2) Date: Sep. 21, 2018

(87) PCT Pub. No.: WO2017/164428
PCT Pub. Date: Sep. 28, 2017

(65) Prior Publication Data
US 2019/0038217 A1    Feb. 7, 2019

(51) Int. Cl.
*A61B 5/00* (2006.01)
*G16H 10/60* (2018.01)
(Continued)

(52) U.S. Cl.
CPC .......... *A61B 5/4839* (2013.01); *A61B 5/0002* (2013.01); *A61B 5/1118* (2013.01);
(Continued)

(58) Field of Classification Search
None
See application file for complete search history.

(56) References Cited

U.S. PATENT DOCUMENTS 6,024,699 A * 2/2000 Surwit ............... G06F 19/3418
                                                    600/300
6,280,380 B1 * 8/2001 Bardy ................. A61B 5/4884
                                                    600/300

(Continued)

FOREIGN PATENT DOCUMENTS

KR      10-1145142 B1     5/2012
KR      10-2012-0122457 A  11/2012

*Primary Examiner* — Brian T Gedeon

(57) ABSTRACT

Provided is a diabetes management method and system. A diabetes management server includes a database defining a monitoring procedure for at least two patient groups. When receiving a blood sugar measurement value from a user terminal, the diabetes management server generates feedback information about the blood sugar measurement value by using a monitoring procedure for a patient group including the user and then transmits the feedback information to the user terminal or the like.

9 Claims, 20 Drawing Sheets

(51) Int. Cl.
*G16H 20/60* (2018.01)
*A61B 5/11* (2006.01)
*A61B 5/145* (2006.01)
*G09B 19/00* (2006.01)
*G16H 40/67* (2018.01)
*G16H 20/30* (2018.01)
*G16H 20/10* (2018.01)
*G16H 40/63* (2018.01)
*G16H 50/30* (2018.01)
*G16H 80/00* (2018.01)

(52) U.S. Cl.
CPC .......... *A61B 5/14532* (2013.01); *A61B 5/486* (2013.01); *A61B 5/4872* (2013.01); *A61B 5/742* (2013.01); *A61B 5/746* (2013.01); *A61B 5/7465* (2013.01); *A61B 5/7475* (2013.01); *G09B 19/0092* (2013.01); *G16H 10/60* (2018.01); *G16H 20/10* (2018.01); *G16H 20/30* (2018.01); *G16H 20/60* (2018.01); *G16H 40/63* (2018.01); *G16H 40/67* (2018.01); *G16H 50/30* (2018.01); *G16H 80/00* (2018.01); *A61B 5/4866* (2013.01)

(56) References Cited

U.S. PATENT DOCUMENTS

| | | | |
|---|---|---|---|
| 2004/0019259 A1* | 1/2004 | Brown | G06F 19/3418 600/300 |
| 2004/0054263 A1* | 3/2004 | Moerman | A61B 5/0002 600/300 |
| 2006/0036134 A1* | 2/2006 | Tarassenko | A61B 5/0022 600/300 |
| 2006/0089542 A1* | 4/2006 | Sands | A61B 5/0022 600/300 |
| 2007/0016127 A1* | 1/2007 | Staib | G01N 33/66 604/66 |
| 2007/0179349 A1* | 8/2007 | Hoyme | G06Q 50/22 600/300 |
| 2007/0231846 A1* | 10/2007 | Cosentino | C12Q 1/006 435/14 |
| 2010/0145173 A1* | 6/2010 | Alferness | G16H 50/50 600/365 |
| 2011/0124996 A1* | 5/2011 | Reinke | G06F 19/3456 600/365 |
| 2013/0226612 A1* | 8/2013 | Carmeli | G16H 70/20 705/3 |
| 2014/0017648 A1* | 1/2014 | Williams | G06F 19/3481 434/238 |
| 2014/0142981 A1* | 5/2014 | Gopal | G16H 50/30 705/3 |
| 2014/0316759 A1* | 10/2014 | Albisser | G16H 50/20 703/11 |
| 2015/0118658 A1* | 4/2015 | Mayou | A61B 5/746 434/127 |
| 2017/0053552 A1* | 2/2017 | Zhong | A61M 5/142 |
| 2017/0076630 A1* | 3/2017 | Angelides | G16H 20/60 |

* cited by examiner

FIG. 3

| PATIENT GROUP | DEFINITION |
|---|---|
| A | PATIENT GROUP CAPABLE OF BEING MANAGED WITHOUT ANTIDIABETIC DRUGS |
| B | PATIENT GROUP CAPABLE OF BEING MANAGED BY ORAL ANTIDIABETIC DRUGS THAT DO NOT CAUSE HYPOGLYCEMIA |
| C | PATIENT GROUP CAPABLE OF BEING MANAGED BY ORAL ANTIDIABETIC DRUGS CAPABLE OF CAUSING HYPOGLYCEMIA |
| D | PATIENT GROUP CAPABLE OF BEING MANAGED BY INSULIN |

310 — A
320 — B
330 — C
340 — D

DIABETES MANAGEMENT METHOD AND SYSTEM FOR SAME

CROSS REFERENCE TO RELATED APPLICATION

This present application is a national stage filing under 35 U.S.C § 371 of PCT application number PCT/KR2016/002846 filed on Mar. 22, 2016. The disclosure of the above-listed application is hereby incorporated by reference in its entirety.

TECHNICAL FIELD

The present disclosure relates to a diabetes management method and system, and more particularly, to a diabetes management method and system for generating and transmitting feedback information for real-time diabetes management to a user by using blood sugar measurement values received from a user terminal.

BACKGROUND ART

Diabetes is a metabolic disorder that causes abnormal function or insufficient secretion of insulin, which results in a symptom in which blood sugar levels are outside the normal range. Diabetes is a complex disease that may affect human body tissues due to complications such as blindness, kidney failure, heart failure, and neuropathy, and the number of diabetic patients is increasing every year.

In the case of diabetes, it is necessary to measure blood sugar levels by using a blood sugar meter and to manage blood sugar levels through suitable means such as diets, exercise programs, insulin injections, and oral antidiabetic drugs.

DESCRIPTION OF EMBODIMENTS

Technical Problem

Provided is a diabetes management method in a diabetes management server that may provide optimal feedback information for each user by using blood sugar measurement values received through a user terminal.

Also provided is a diabetes management method in a user terminal that may automatically measure a blood sugar level of a user, receive feedback information thereof, and provide the feedback information to the user.

Solution to Problem

According to an aspect of the present disclosure, as an example of a diabetes management method of a diabetes management server, there is provided a diabetes management method of a diabetes management server connected to a user terminal through a wired/wireless communication network, the diabetes management server including a database defining a monitoring procedure for at least two patient groups, the diabetes management method including: receiving a blood sugar measurement value from the user terminal; detecting, from the database, a monitoring procedure for a patient group including the user; generating feedback information about the blood sugar measurement value by using the detected monitoring procedure; and transmitting the generated feedback information to at least one of the user terminal, a carer terminal of the user, a call center, and a medical staff terminal.

According to another aspect of the present disclosure, as an example of a diabetes management method of a user terminal, there is provided a diabetes management method of a user terminal connected to a blood sugar meter through short-range wireless communication, the user terminal including an automatic mode for receiving a blood sugar measurement value from the blood sugar meter and a manual mode for providing an interface screen for inputting/receiving a blood sugar measurement value from a user, the diabetes management method including: transmitting, to a diabetes management server, blood sugar measurement time information together with a blood sugar measurement value acquired through the automatic mode or the manual mode; and receiving, from the diabetes management server, and displaying feedback information generated based on the blood sugar measurement time and the blood sugar measurement value, by using a predetermined monitoring procedure for a patient group including a user.

Advantageous Effects of Disclosure

According to the present disclosure, the user may receive proper care in real time by transmitting the value measured through the blood sugar meter to the diabetes management server through the user terminal and receiving the feedback information thereof. Also, the optimal feedback information about the blood sugar measurement value for each blood sugar measurement time may be provided according to the monitoring procedure defined for each patient group including each user. Also, when an insulin dose increase/decrease according to the blood sugar measurement value of the user is outside a predetermined range, a message may be transmitted to the medical staff terminal to take a proper action, and when the user is in a dangerous situation such as hypoglycemia or hyperglycemia, a call may be made through the call center or a message may be transmitted to the carer terminal to properly protect an urgent patient. Also, information for exercise management and diet management necessary for diabetes management may be provided together.

BRIEF DESCRIPTION OF DRAWINGS

FIG. 3 is a table illustrating an example of patient groups according to the present disclosure.

MODE OF DISCLOSURE

Hereinafter, diabetes management methods and systems according to the present disclosure will be described in detail with reference to the accompanying drawings.

Figure 1:
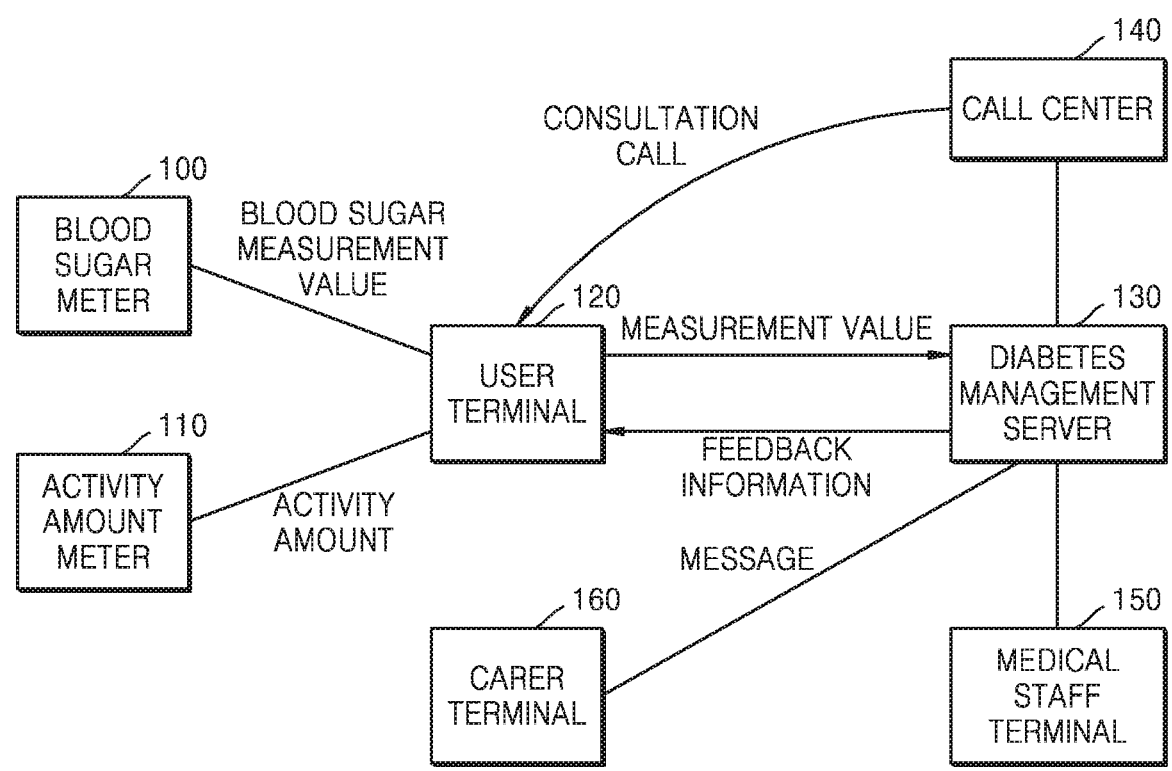
FIG. 1 is a diagram illustrating a schematic structure of a diabetes management system according to the present disclosure.

FIG. 1 is a diagram illustrating a schematic structure of a diabetes management system according to the present disclosure.

Referring to FIG. 1, an entire diabetes management system may include a blood sugar meter 100, an activity amount meter 110, a user terminal 120, a diabetes management server 130, a call center 140, a medical staff terminal 150, and a carer terminal 160.

The blood sugar meter 100 may measure a blood sugar of a user and transmit a blood sugar measurement value through wired/wireless communication. As an example, the blood sugar meter may include a short-range communication module such as Bluetooth and transmit a blood sugar measurement value to the user terminal through Bluetooth. As another example, the blood sugar meter 100 may be implemented in various forms such as a form attached to a human body or a form inserted into a human body.

The activity amount meter 110 may measure an activity amount of the user and transmit the measured activity amount through wired/wireless communication. The activity amount meter 110 may include various sensors and use the sensors to detect the movement degree, the number of steps, or the heart rate, the body temperature, or the like of the user. For example, the activity amount meter 110 may convert the activity amount into calories. The activity amount meter 110 may transmit the activity amount to the user terminal through short-range wireless communication such as Bluetooth.

The user terminal 120 may receive the blood sugar measurement value or the activity amount and transmit the same to the diabetes management server 130, and may receive various feedback information for blood sugar management, diet management, or exercise management from the diabetes management server 130. The blood sugar measurement value or the activity amount may be automatically input to the user terminal 120 through the blood sugar meter 100 or the activity amount meter 110, or may be manually input by the user.

Examples of the user terminal 120 may include various terminals capable of wired and wireless communication such as smart phones or tablet personal computers (PCs), as well as a dedicated terminal for diabetes management. For example, when the user terminal 120 is a smart phone, the configuration according to the present disclosure may be implemented as an application (app) and installed in the smart phone.

When receiving various data including the blood sugar measurement value, the activity amount, diet information, or exercise information from the user terminal 120, the diabetes management server 130 may generate feedback information about blood sugar management, diet management, or exercise management according to a certain monitoring procedure and transmit the same to the user terminal 120, the call center 140, the medical staff terminal 150, or the carer terminal 160.

For example, when the blood sugar measurement value is within a certain range, the diabetes management server 130 may transmit the feedback information to the user terminal 120. However, when the blood sugar measurement value is hypoglycemia or hyperglycemia, the diabetes management server 130 may transmit feedback information for requesting a consultation call to the call center 140 or transmit a message to the carer terminal 160 in order to determine the user's condition.

The medical staff terminal 150 may access the diabetes management server 130 to inquire blood sugar information, diet information, or exercise information about each user. For example, when the diabetes management server 130 generates feedback information about an insulin increase/decrease for the user requiring an insulin prescription and transmits the feedback information to the user terminal 120, if the insulin increase/decrease is outside a predetermined range, the diabetes management server 130 may transmit an emergency message to the medical staff terminal 150 to enable consultation and management. The medical staff terminal 150 may be in various forms such as a computer or a portable terminal such as a smart phone.

Figure 2:
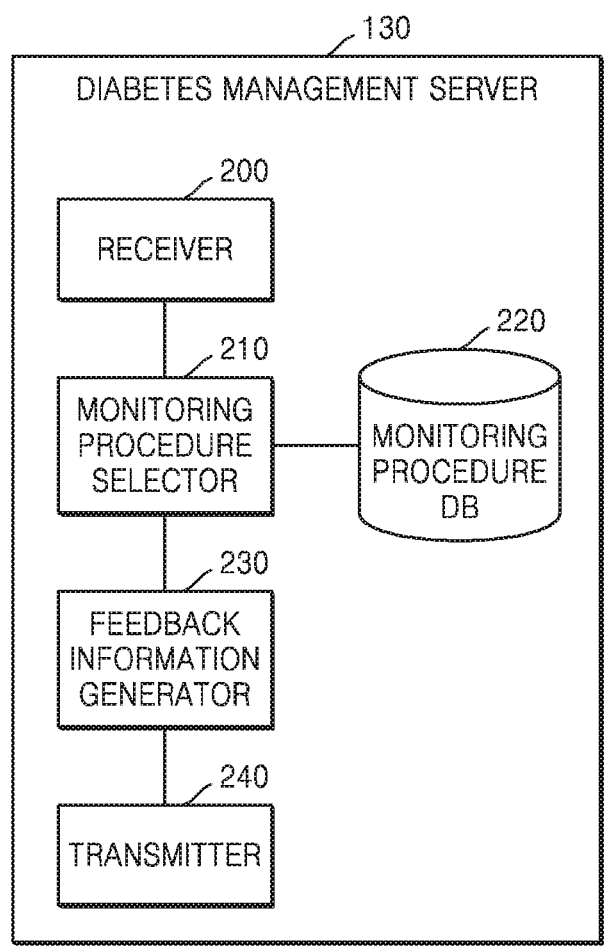
FIG. 2 is a diagram illustrating a configuration of an embodiment of a diabetes management server according to the present disclosure.

FIG. 2 is a diagram illustrating a configuration of an embodiment of a diabetes management server according to the present disclosure.

Referring to FIG. 2, the diabetes management server 130 may include a receiver 200, a monitoring procedure selector 210, a monitoring procedure database (DB) 220, a feedback information generator 230, and a transmitter 240.

The receiver 200 may receive the blood sugar measurement value, the activity amount, the diet information, or the exercise information of the user from the user terminal.

The monitoring procedure selector 210 may detect a monitoring procedure for a patient group including the user from the monitoring procedure DB 220. The diabetes management server 130 may prestore information about which patient group the user belongs to.

For example, the receiver 200 may receive terminal identification information such as a telephone number of the user terminal or user identification information (e.g., patient code) together with the blood sugar measurement value, and the monitoring procedure selector 210 may detect a patient group including the user from the prestored information by using the terminal identification information or the user identification information and then extract a monitoring procedure for the detected patient group from the monitoring procedure DB 220.

The monitoring procedure DB 220 may define and store a monitoring procedure for each patient group. The monitoring procedures may also be classified according to the blood sugar measurement times. For example, the monitoring procedures may be different according to whether the blood sugar measurement time is before or after a meal.

The patient groups may include at least two groups according to embodiments. Although FIG. 3 illustrates an example in which the patient groups are classified into four groups, the present disclosure is not limited thereto. For example, the patient groups may be classified into various types according to embodiments and then a proper monitoring process may be defined according to the blood sugar measurement time for each patient group. An example of the monitoring procedure for each patient group in FIG. 3 will be described with reference to FIGS. 5 to 9.

The feedback information generator 230 may generate feedback information for blood sugar management, exercise management, or diet management based on the blood sugar measurement time and the blood sugar measurement value by using the monitoring procedure selected by the monitoring procedure selector 210. For example, the feedback information generator 230 may generate various warnings or guide messages about the blood sugar, determine various programs for diet management, or determine various programs for exercise management.

The transmitter 240 may transmit the feedback information to the user terminal, the call center, the carer terminal, or the medical staff terminal according to the type and feature of the feedback information generated by the feedback information generator 230.

FIG. 3 is a diagram illustrating an example of patient groups according to the present disclosure.

Referring to FIG. 3, the patient groups may include a patient group A 310 capable of being managed without antidiabetic drugs, a patient group B 320 capable of being managed by oral antidiabetic drugs that do not cause hypoglycemia, a patient group C 330 capable of being managed by oral antidiabetic drugs capable of causing hypoglycemia, and a patient group D 340 capable of being managed by insulin.

Hereinafter, the patient groups of FIG. 3 will be described for convenience of description; however, the classification of patient groups may be variously modified according to embodiments as described above.

Figure 4:
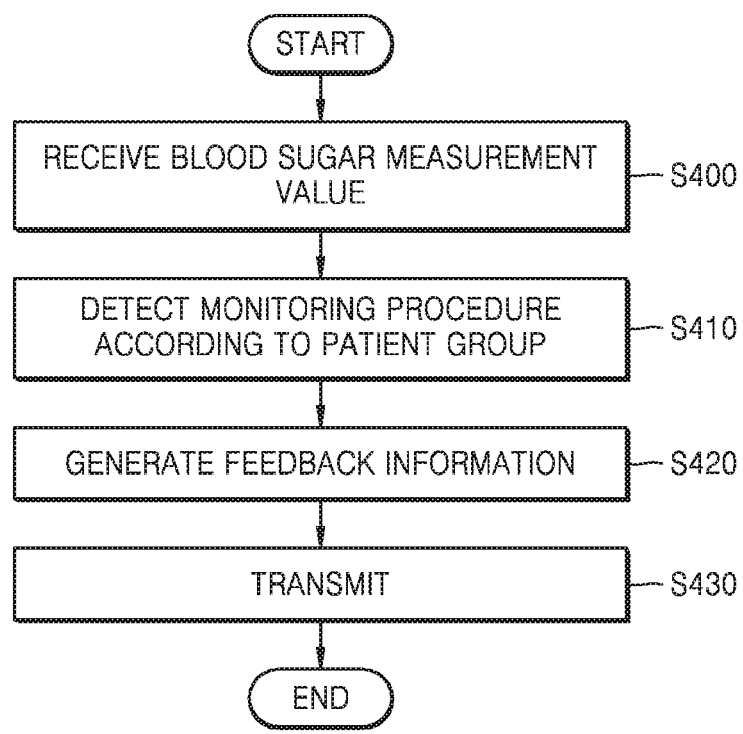
FIG. 4 is a flowchart illustrating an example of a diabetes management method in a diabetes management server, according to the present disclosure.

FIG. 4 is a flowchart illustrating an example of a diabetes management method in a diabetes management server according to the present disclosure.

Referring to FIG. 4, the diabetes management server may receive a blood sugar measurement time and a blood sugar measurement value from the user terminal (S400). It is assumed that the diabetes management server prestores various information about the user such as the user's name, age, sex, telephone number, the telephone number of the carer terminal, the disease name, the prescription, the patient group information to which the user belongs, or the patient code. Thus, the diabetes management server may detect the patient group including the user based on the identification information (terminal identification information or user identification information) received together with the blood sugar measurement value and detect a monitoring procedure for the detected patient group from the database (S410).

The diabetes management server may generate feedback information about the blood sugar measurement value by applying a monitoring procedure corresponding to the blood sugar measurement time in the monitoring procedure for the patient group including the user (S420). For example, when the user belongs to the patient group A, the diabetes management server may detect a monitoring procedure for the patient group A and generate feedback information about the blood sugar measurement value according to a preprandial monitoring procedure when the blood sugar measurement time is before a meal.

The diabetes management server may transmit the generated feedback information to at least one of the user terminal, the carer terminal, the call center, and the medical staff terminal (S430). For example, when the user blood sugar measurement value is within a certain range, the diabetes management server may transmit various information or warning messages according to the blood sugar measurement values only to the user terminal. However, in a dangerous situation such as hyperglycemia or hypoglycemia, the diabetes management server may generate a notification message as feedback information and transmit the same to the carer terminal or may generate feedback information for a consultation request and transmit the same to the call center. As another example, when the patient group D 340 of FIG. 3 is hypoglycemic and thus the increase of an insulin dose is necessary, if the increase of the insulin dose is outside a predetermined range, the diabetes management server may notify the fact to the medical staff terminal to enable consultation or management.

Figure 5:
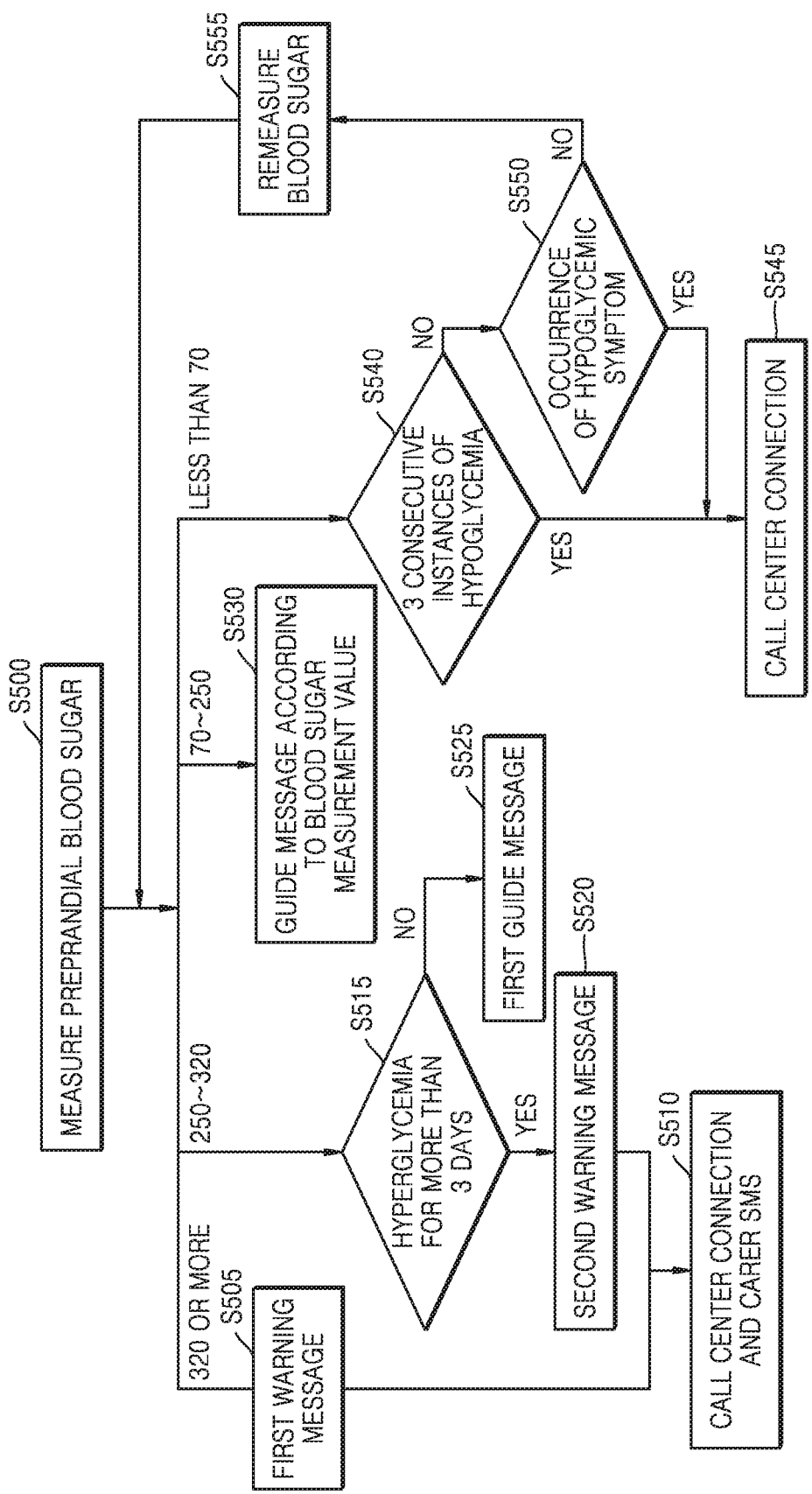
FIGS. 5 to 9 are flowcharts illustrating an example of a monitoring procedure for each patient group, according to the present disclosure.
Figure 6:
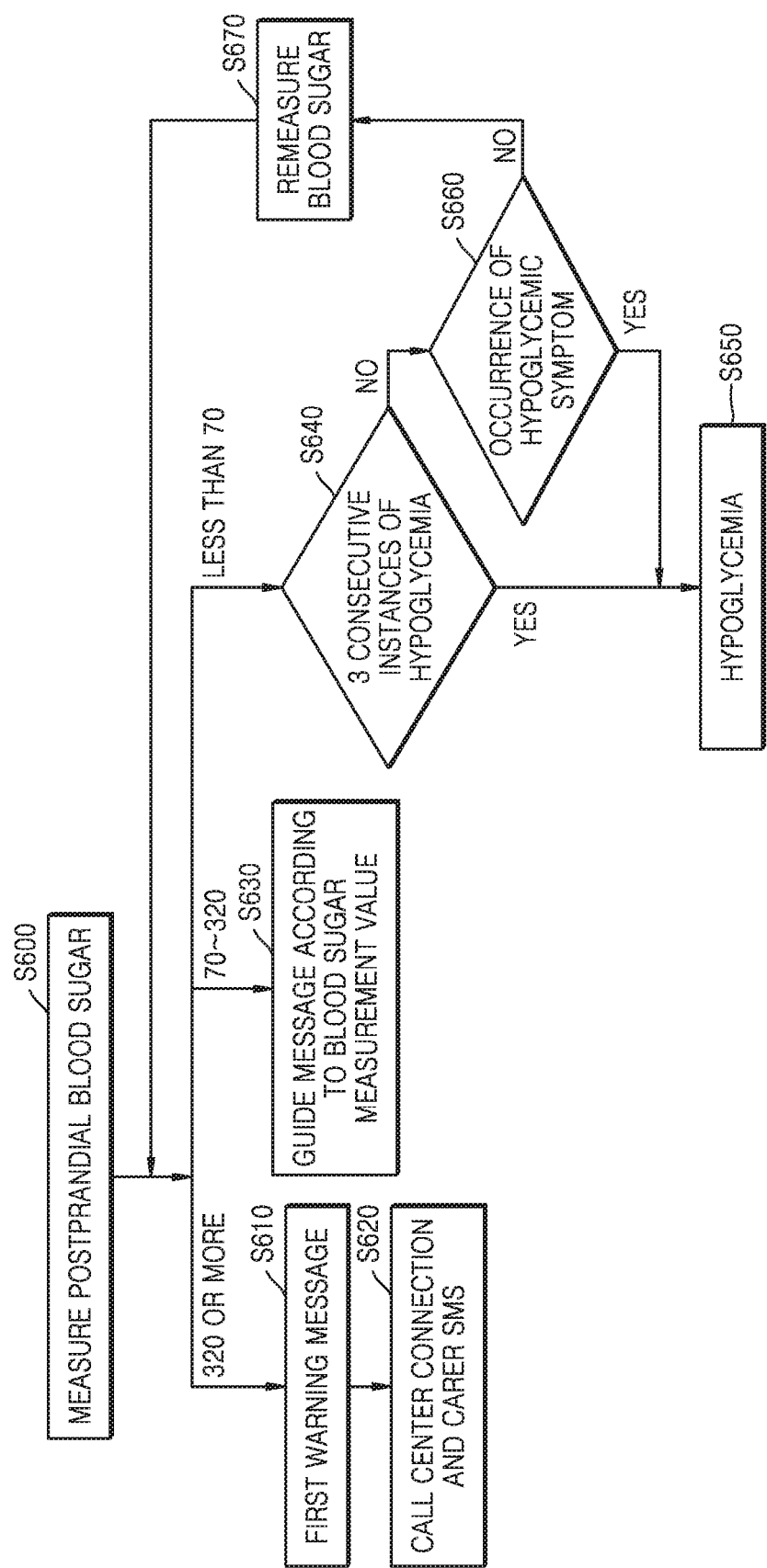
Figure 7:
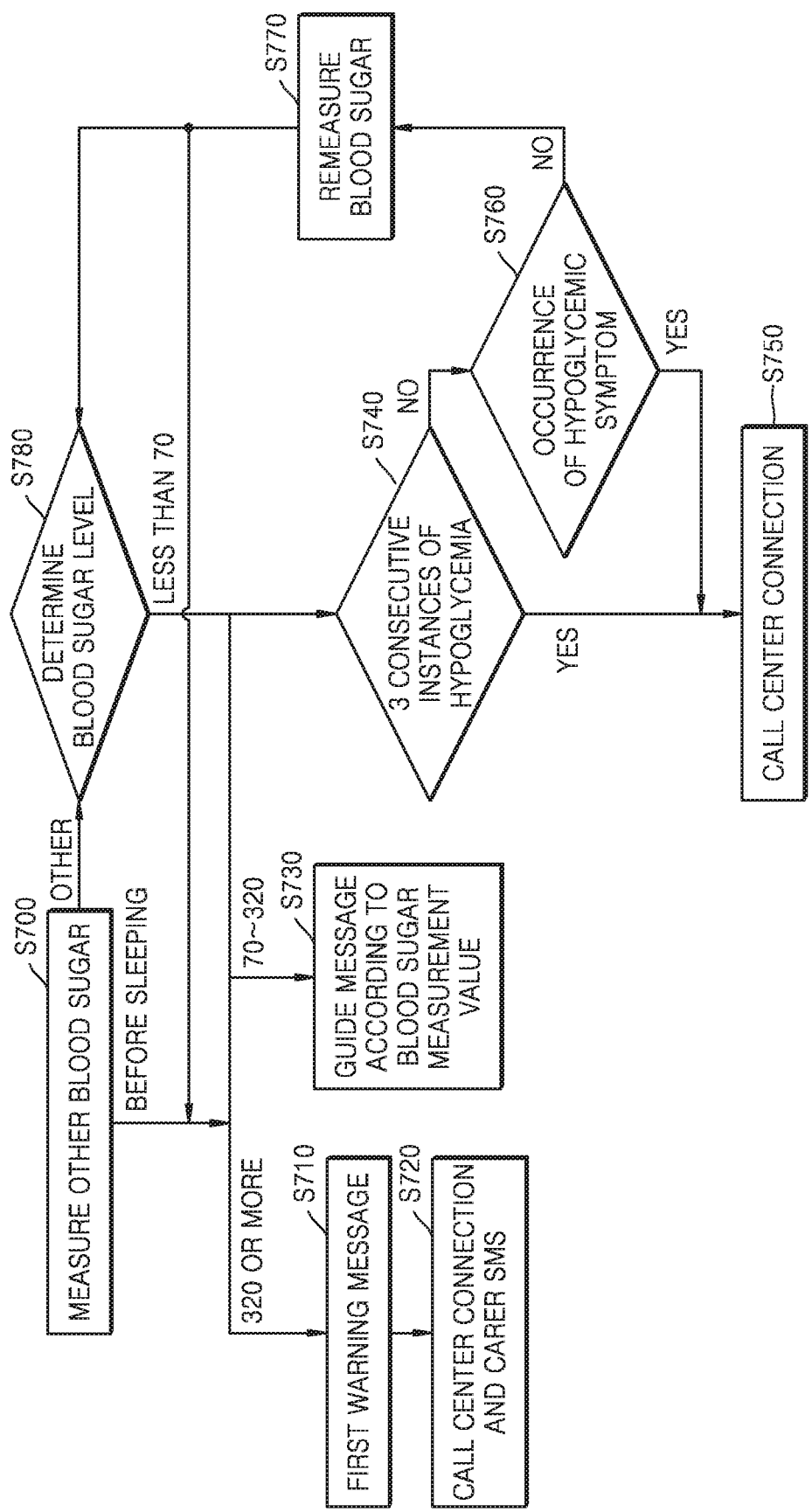
Figure 8:
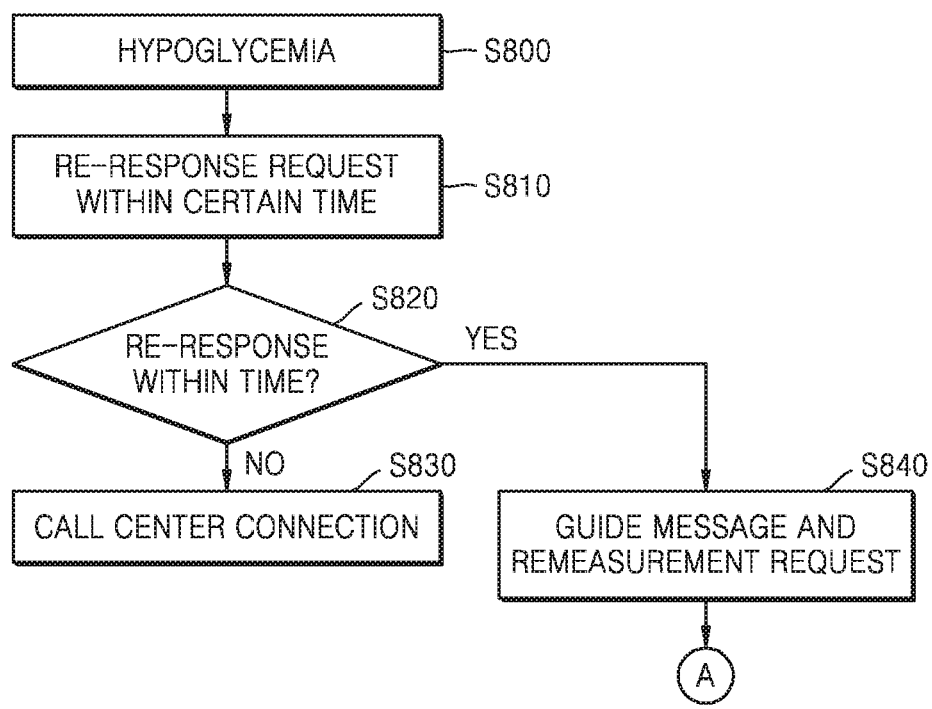
Figure 9:
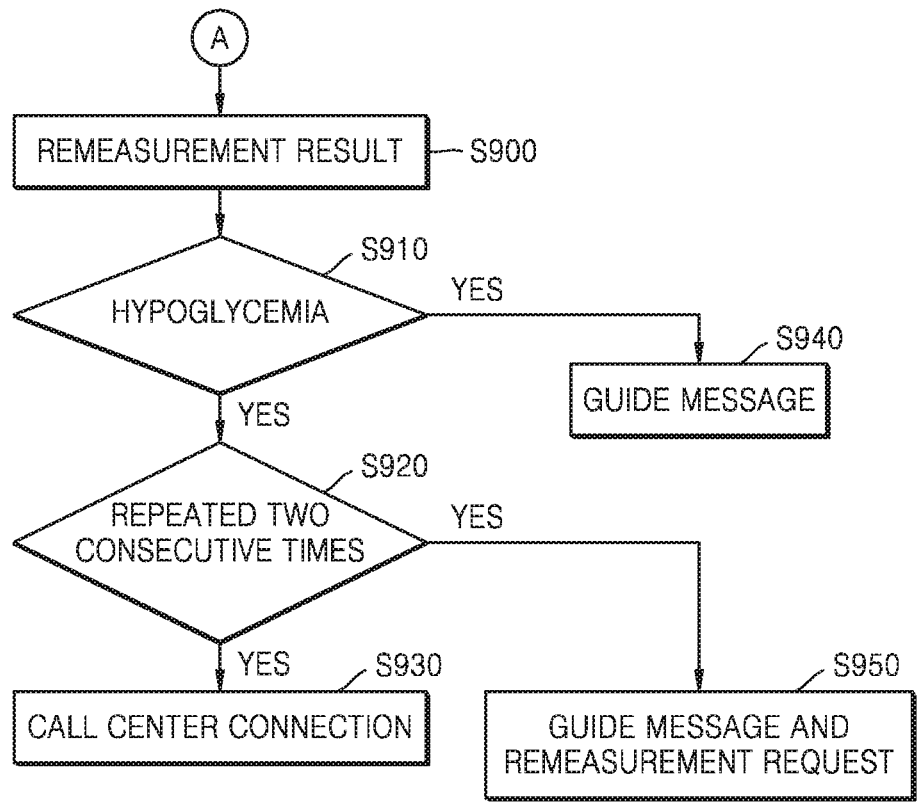

FIGS. 5 to 9 are diagrams illustrating an example of a monitoring procedure for each patient group according to the present disclosure. For convenience of description, FIGS. 5 to 7 illustrate a monitoring procedure for the patient group A, and FIGS. 8 and 9 illustrate a monitoring procedure when the patient group C is in hypoglycemia.

According to embodiments, the monitoring procedure of FIGS. 5 to 7 may also be applied to the patient group B, and the configuration of FIGS. 5 to 7 except the monitoring procedure of hypoglycemia may also be applied to the patient groups C and D. For example, for the patient group C, the monitoring procedure of a hypoglycemic portion of FIGS. 5 to 7 may be replaced with the monitoring procedure of FIGS. 8 and 9.

FIGS. 5 to 9 illustrate an example of a monitoring procedure for each blood sugar measurement time of a patient group in order to facilitate an understanding of the present disclosure. However, the present disclosure is not limited thereto, and various patient groups and various monitoring procedures according to the blood sugar measurement times for the respective patient groups may be defined and used.

First, FIG. 5 is a flowchart illustrating an example of a monitoring procedure for a preprandial blood sugar measurement value according to the present disclosure.

Referring to FIG. 5, the diabetes management server may receive a preprandial blood sugar measurement value of the user belonging to the patient group A from the user terminal (S500).

When the blood sugar measurement value is 320 or more, the diabetes management server may generate a first warning message for warning of a blood sugar risk level and indicating connection to the call center as feedback information and transmits the same to the user terminal (S505). Then, the diabetes management server may transmit feedback information for a consultation request to the call center and transmit a message indicating a blood sugar risk to the carer terminal (S510).

When the blood sugar measurement value is between 250 and 320, the diabetes management server may determine whether hyperglycemia has continued for more than 3 days (S515). When the hyperglycemia has continued for more than 3 days, the diabetes management server may generate a second warning message indicating that the hyperglycemia has continued for more than 3 days as feedback information and transmit the same to the user terminal (S520). Then, the diabetes management server may transmit feedback information for a consultation request to the call center and transmit a message indicating a blood sugar risk to the carer terminal (S510). When the hyperglycemia has not continued for more than 3 days, the diabetes management server may generate a first guide message indicating that a fasting blood sugar level needs to be checked the next day and transmit the first guide message to the user terminal (S525).

When the blood sugar measurement value is between 70 and 250, the diabetes management server may generate a guide or an encouragement message indicating that the blood sugar measurement value is high or low and transmit the same to the user terminal (S530).

When the blood sugar measurement value is less than 70, the diabetes management server may determine whether hypoglycemia has occurred three consecutive times (S540). When hypoglycemia has occurred three consecutive times, the diabetes management server may transmit feedback information for a consultation request to the call center (S545). Then, the call center may call the user or his or her carer to check the user's condition. Otherwise, when hypoglycemia has not occurred three consecutive times, the diabetes management server may generate feedback information for inquiring whether there is a hypoglycemic symptom such as sweating on the hands, palpitation, or dizziness and transmit the feedback information to the user terminal and wait for a response (S550). When receiving a response indicating that there is a hypoglycemic symptom from the user terminal, the diabetes management server may transmit feedback information for a consultation request to the call center (S545), and when receiving a response indicating that there is no hypoglycemic symptom, the diabetes management server may transmit a guide message for blood sugar remeasurement to the user terminal and receive a blood sugar remeasurement value (S555).

FIG. 6 is a flowchart illustrating an example of a monitoring procedure for a postprandial blood sugar measurement value among monitoring procedures for patient groups according to the present disclosure.

Referring to FIG. 6, the diabetes management server may receive a postprandial blood sugar measurement value of the user belonging to the patient group A from the user terminal (S600).

When the blood sugar measurement value is 320 or more, the diabetes management server may generate a first warning message for warning of a blood sugar risk level and indicating connection to the call center as feedback information and transmits the same to the user terminal (S610). Then the diabetes management server may transmit feedback information for a consultation request to the call center and transmit a message indicating a blood sugar risk to the carer terminal (S620).

When the blood sugar measurement value is between 70 and 320, the diabetes management server may generate a guide or an encouragement message indicating that the blood sugar measurement value is high or low and transmit the same to the user terminal (S630).

When the blood sugar measurement value is less than 70, the diabetes management server may determine whether hypoglycemia has occurred three consecutive times (S640). When hypoglycemia has occurred three consecutive times, the diabetes management server may transmit feedback information for a consultation request to the call center (S650). Then, the call center may call the user or his or her carer to check the user's condition. Otherwise, when hypoglycemia has not occurred three consecutive times, the diabetes management server may generate feedback information for inquiring about a hypoglycemic symptom and transmit the feedback information to the user terminal and wait for a response (S660). When receiving a response indicating that there is a hypoglycemic symptom from the user terminal, the diabetes management server may transmit feedback information for a consultation request to the call center (S650), and when receiving a response indicating that there is no hypoglycemic symptom, the diabetes management server may transmit a guide message for blood sugar remeasurement to the user terminal and receive a blood sugar remeasurement value (S670).

FIG. 7 is a flowchart illustrating an example of a monitoring procedure for blood sugar measurement values in other situations other than preprandial/postprandial situations among monitoring procedures for patient groups according to the present disclosure.

Referring to FIG. 7, the diabetes management server may receive a blood sugar measurement time (e.g., before/after sleeping or before/after exercise) and a blood sugar measurement value from the user terminal (S700).

When the blood sugar measurement time is before sleeping, the diabetes management server may perform a process of transmitting a warning or a guide message according to the blood sugar measurement value (S710 to S770). This process is the same as the process of FIG. 6 and thus redundant descriptions will be omitted for conciseness.

When the blood sugar measurement time is other than "before sleeping" (S780), the diabetes management server may determine the blood sugar level and determine whether hypoglycemia of less than 70 has occurred three consecutive times (S740). When hypoglycemia has occurred three consecutive times, the diabetes management server may transmit feedback information for a consultation request to the call center (S750). Then, the call center may call the user or his or her carer to check the user's condition. Otherwise, when hypoglycemia has not occurred three consecutive times, the diabetes management server may generate feedback information for inquiring about a hypoglycemic symptom and transmit the feedback information to the user terminal and wait for a response (S760). When receiving a response indicating that there is a hypoglycemic symptom from the user terminal, the diabetes management server may transmit feedback information for a consultation request to the call center (S750), and when receiving a response indicating that there is no hypoglycemic symptom, the diabetes management server may transmit a guide message for blood sugar remeasurement to the user terminal and receive a blood sugar remeasurement value (S770).

FIGS. 8 and 9 are flowcharts illustrating an example of a monitoring procedure in a hypoglycemic situation of the patient groups C and D of FIG. 3 among monitoring procedures for patient groups according to the present disclosure.

Referring to FIG. 8, when the blood sugar measurement value received from the user terminal is hypoglycemia of less than 70 and the user belongs to the patient group C or D (S800), the diabetes management server may generate feedback information for requesting a re-response within a certain time (e.g., 1 minute) and transmit the feedback information to the user terminal in order to check whether the user is conscious (S810).

When there is no response from the user terminal within a predetermined certain time (S820), the diabetes management server may generate feedback information for a call consultation request of the call center and feedback information for notifying an emergency to the carer terminal and transmit the same to the call center and the carer terminal respectively (S830).

When there is a response from the user terminal within a predetermined certain time (S820), the diabetes management server may transmit a guide message including a method for raising the blood sugar level to a normal range (e.g., a guide to intake of juice, milk, block sugar, or candy), transmit an inquiry for checking the cause of hypoglycemia (see FIG. 15) to the user terminal, and transmit feedback information for requesting remeasurement after a certain time to the user terminal (S840). The diabetes management server may periodically transmit the remaining time until remeasurement to the user terminal.

Referring to FIG. 9, when receiving a blood sugar remeasurement value from the user terminal (S900), the diabetes management server may check the blood sugar measurement value and transmit a guide message about a current blood sugar state to the user terminal when the blood sugar measurement value does not correspond to hypoglycemia (S940). When the remeasurement value is still in hypoglycemia (S910), since the user has not yet escaped from hypoglycemia, the diabetes management server may transmit a notice such as "food intake" for overcoming hypoglycemia to the user terminal and request remeasurement again after a certain time (S950). When the remeasurement values correspond to hypoglycemia two consecutive times (S920), the diabetes management server may transmit a message indicating that the blood sugar is not recovered to the user terminal, transmit feedback information of a consultation request to the call center, and transmit a notification message to the carer terminal (S930).

Figure 10:
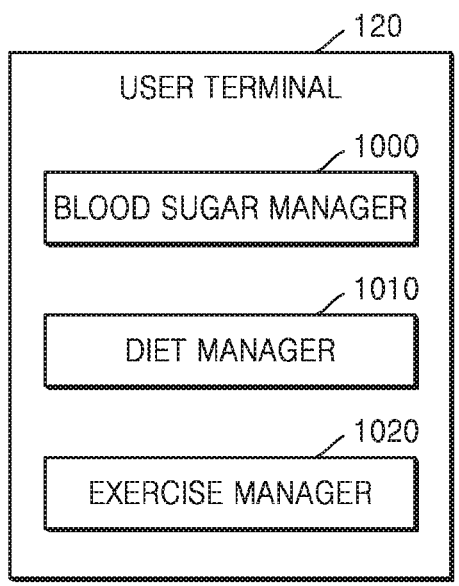
FIG. 10 is a diagram illustrating a configuration of an embodiment of a user terminal including a diabetes management method, according to the present disclosure.

FIG. 10 is a diagram illustrating a configuration of an embodiment of a user terminal including a diabetes management method according to the present disclosure.

Referring to FIG. 10, the user terminal 120 may include a blood sugar manager 1000, a diet manager 1010, and an exercise manager 1020.

The blood sugar manager 1000 may receive the blood sugar measurement value through an automatic mode for receiving the blood sugar measurement value from the blood sugar meter and a manual mode for providing an interface screen for inputting the blood sugar measurement value by the user and transmit the received blood sugar measurement value to the diabetes management server. The blood sugar manager may transmit information about the blood sugar measurement time (e.g., before/after a meal, before sleeping, or before/after exercise) to the diabetes management server together with the blood sugar measurement value.

The blood sugar manager 1000 may receive feedback information about the blood sugar measurement value for each blood sugar measurement time from the diabetes management server. The feedback information about the blood sugar measurement value for each blood sugar measurement time is not the same for all users, but may be different from each other through the application of different monitoring procedures according to the patient groups to which the users belongs.

The diet manager 1010 may receive, store, and manage the food calorie intake of the user and provide a diet management program for diet management based on the food calorie intake of the user. A particular method of diet management will be described with reference to FIG. 11.

The exercise manager 1020 may receive an activity amount from the activity amount meter, store and manage the activity amount, and provide an exercise management program reflecting the exercise possibility and the presence/absence of a complication of the user. A particular method of exercise management will be described with reference to FIG. 12.

Figure 11:
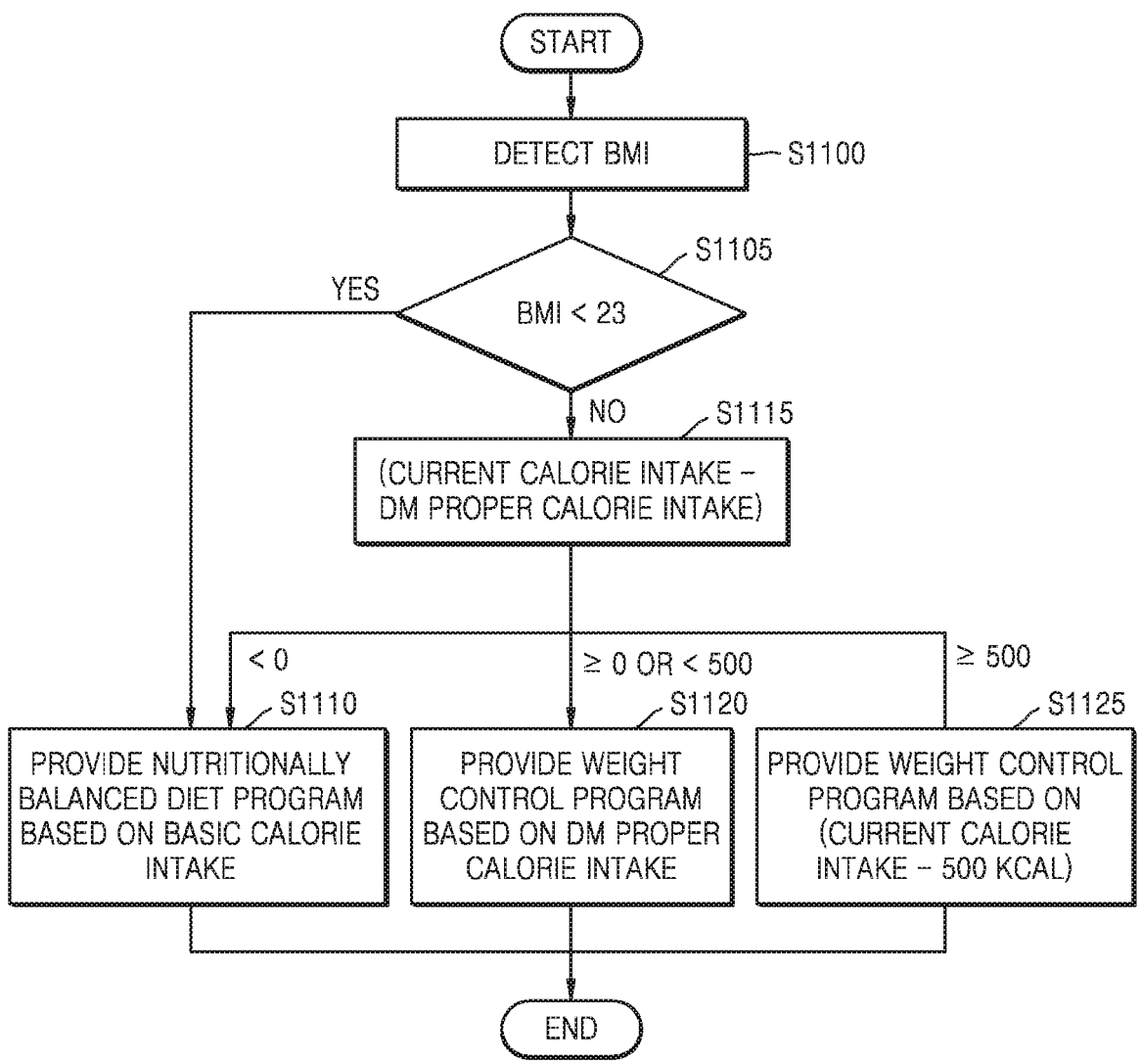
FIG. 11 is a flowchart illustrating an example of a method of providing a diet program for diabetes management, according to the present disclosure.

FIG. 11 is a diagram illustrating an example of a method of providing a diet program for diabetes management according to the present disclosure.

Referring to FIG. 11, the diabetes management server may receive the current (or existing) calorie intake of the user from the user terminal and detect a body mass index of the user (BMI) (S1100). When the body mass index of the user is less than a first threshold value (e.g., 23), the diabetes management server may provide a nutritionally balanced diet program based on the current calorie intake of the user (S1110).

When the body mass index of the user is equal to or greater than the first threshold value (S1105) and the current calorie intake is less than a proper calorie intake amount (DM proper calorie intake) of a diabetic patient (S1115), the diabetes management server may provide a nutritionally balanced diet program based on the current calorie intake to the user terminal (S1110). When the current calorie intake is greater than the DM proper calorie intake and smaller than a second threshold value (e.g., 500), the diabetes management server may provide a weight control program based on the DM proper calorie intake (S1120). When the current calorie intake is greater than the DM proper calorie intake by the second threshold value or more, the diabetes management server may provide a weight control program based on the calorie value obtained by subtracting the second threshold value from the current calorie intake (S1125).

Although the diabetes management server determines and provides a diet program suitable for the user in the present embodiment, the present disclosure is not limited thereto and the user terminal may select and provide a diet program through the above method.

Figure 12:
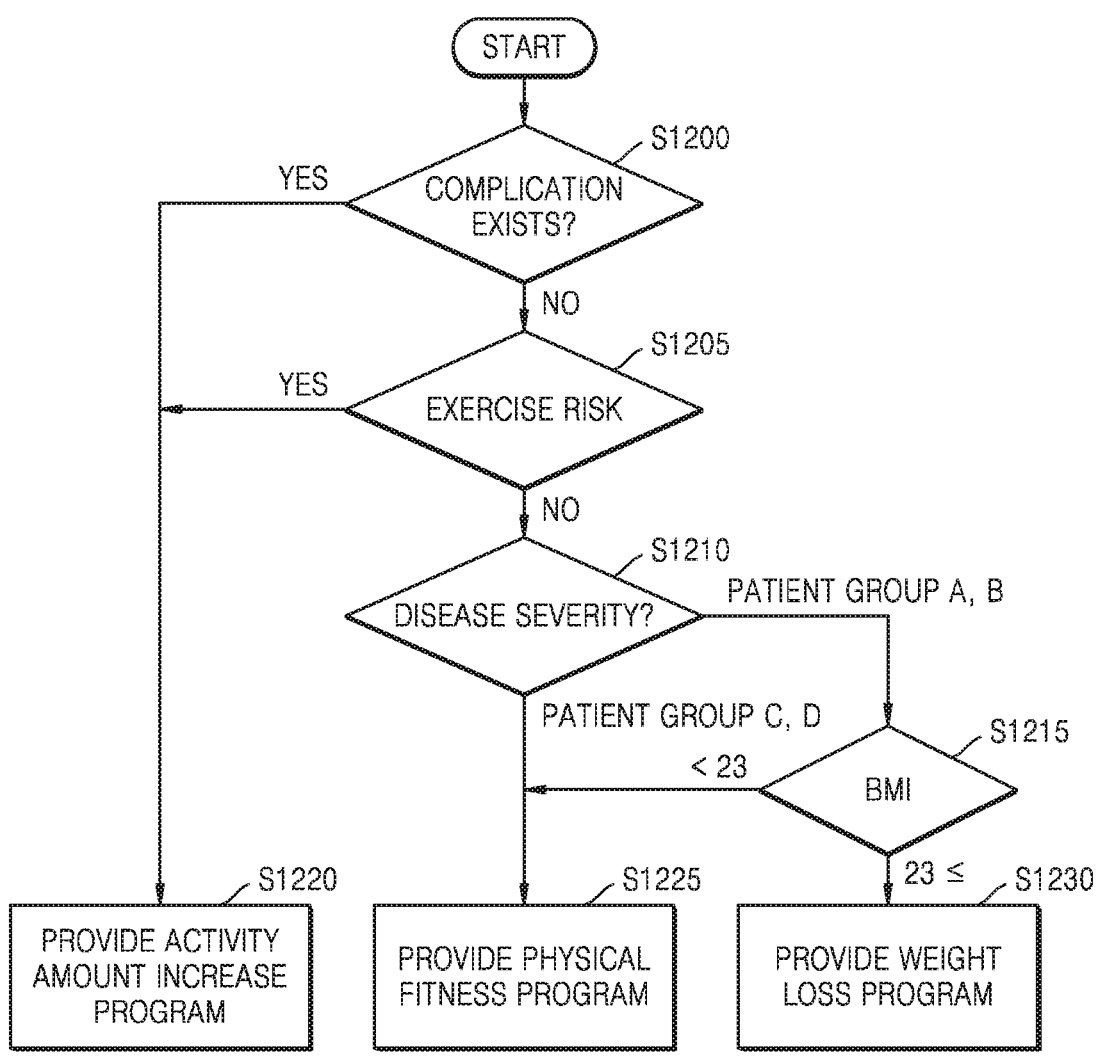
FIG. 12 is a flowchart illustrating an example of a method of providing an exercise program for diabetes management, according to the present disclosure.

FIG. 12 is a diagram illustrating an example of a method of providing an exercise program for diabetes management according to the present disclosure.

Referring to FIG. 12, the diabetes management server may determine whether the user has a complication or belongs to an exercise risk group through the prestored user information (S1200 and S1205). When the user has a complication or should be restricted in exercise, the diabetes management server may select and provide an activity amount increase program (S1220).

In the case of the user that has no complication and may exercise, the diabetes management server may provide different exercise programs according to the relative seriousness of diabetes. For example, if the patient groups are classified into four groups A to D as illustrated in FIG. 3, when the user belongs to the patient group C or D, the diabetes management server may select and provide a physical fitness program (S1225). When the user belongs to the patient group A or B (S1210), the diabetes management server may provide a physical fitness program or a weight loss program (S1225 and S1230) according to the body mass index of the user (S1215).

Although the diabetes management server determines and provides an exercise program suitable for the user in the present embodiment, the present disclosure is not limited thereto and the user terminal may select and provide an exercise program through the above method.

Figure 15:
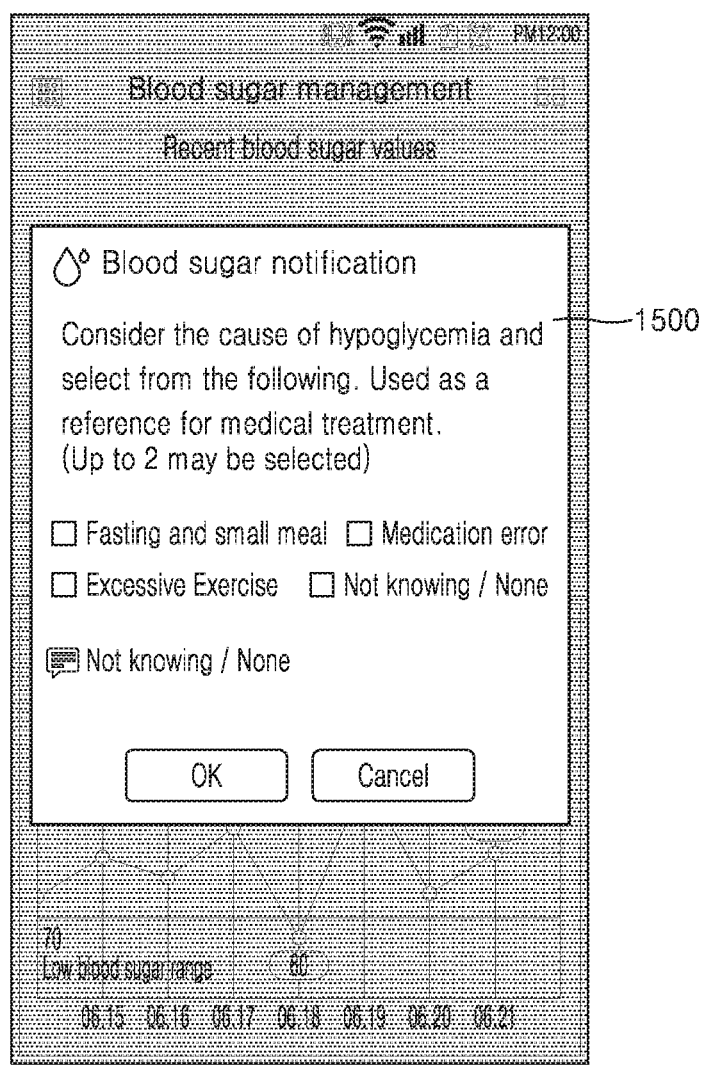
Figure 16:
Figure 17:
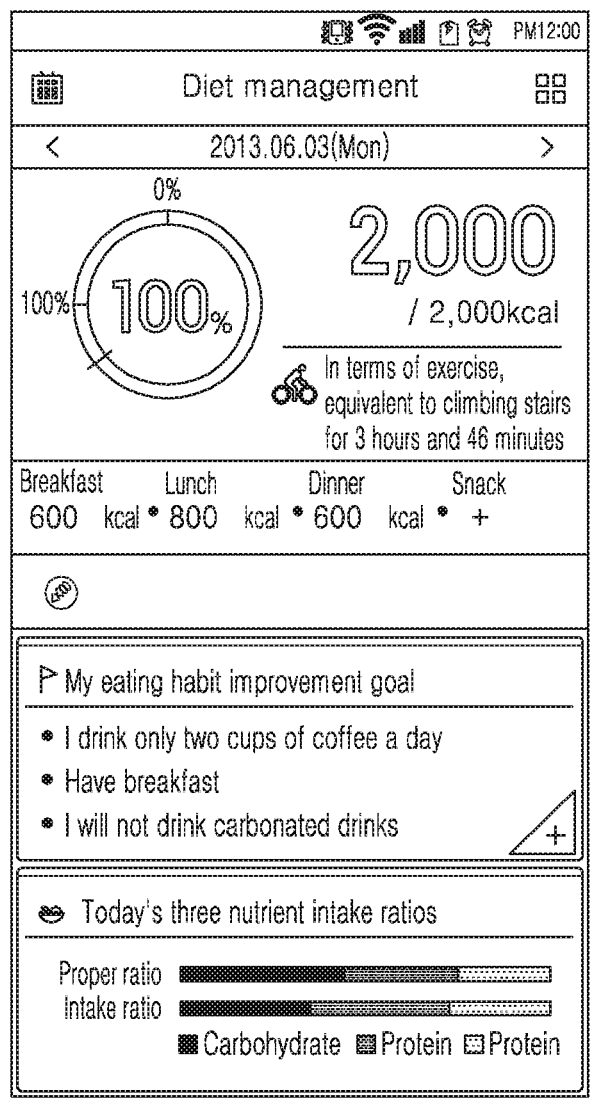
Figure 18:
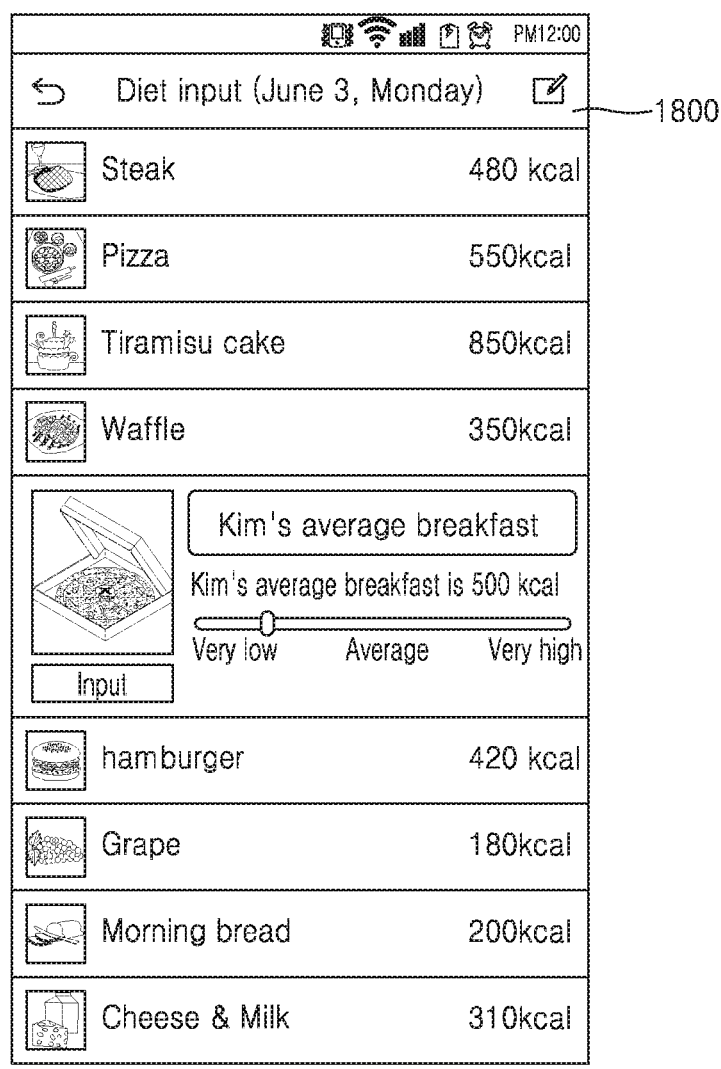
Figure 19:
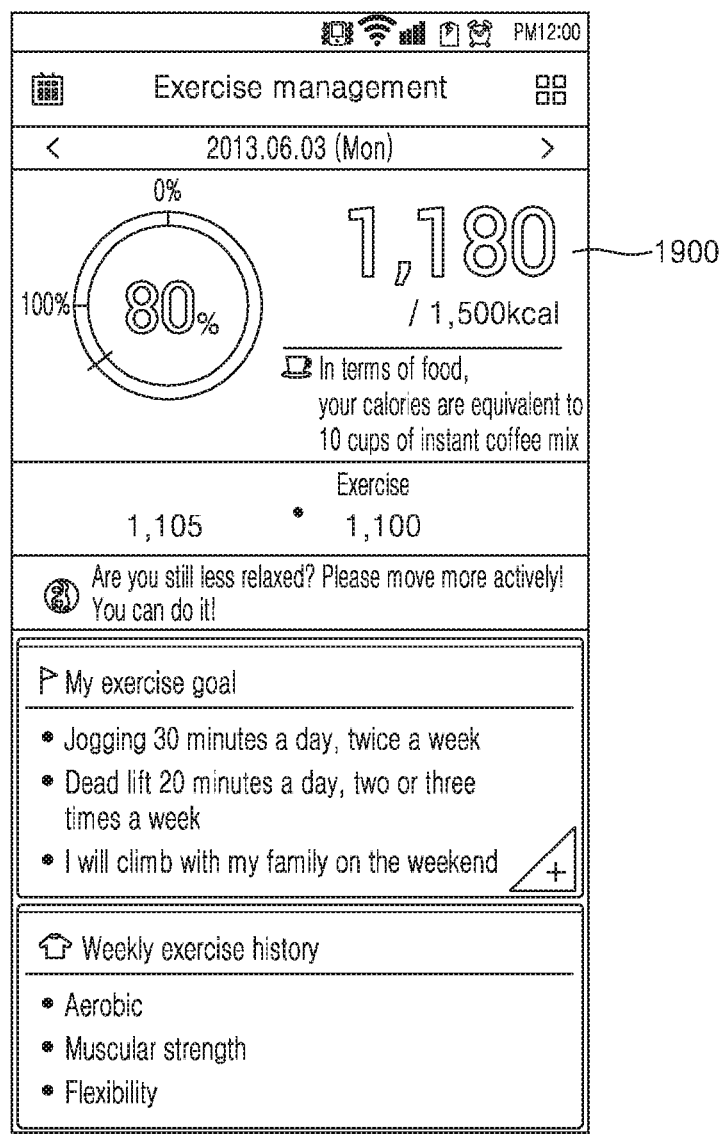
Figure 20:
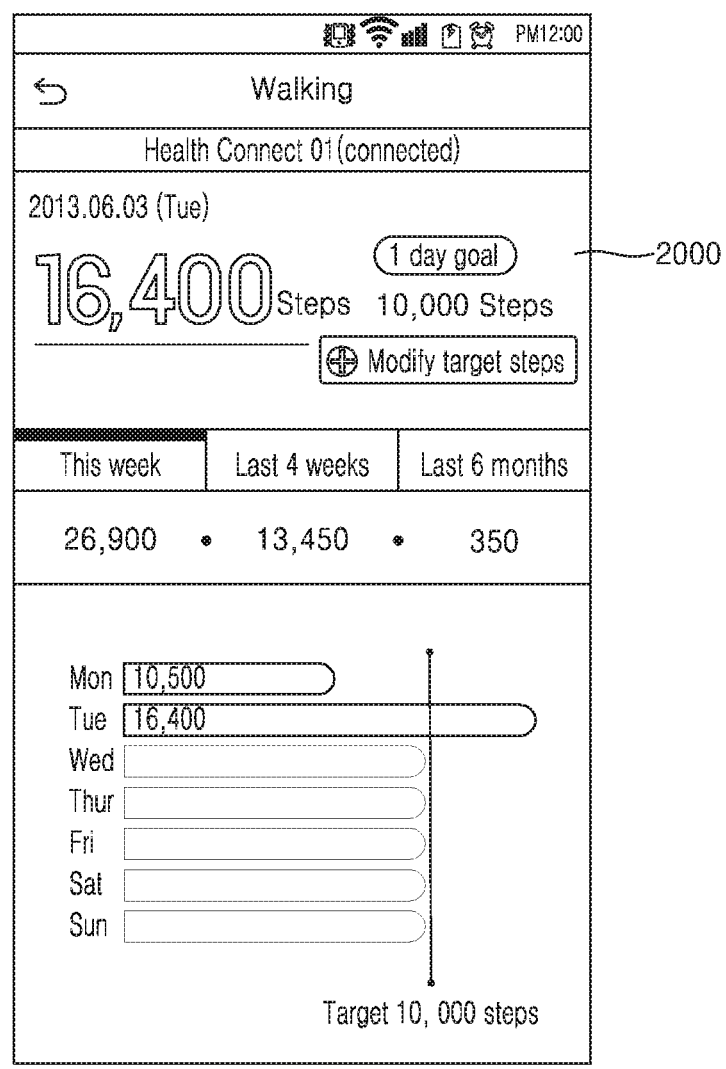
Figure 21:
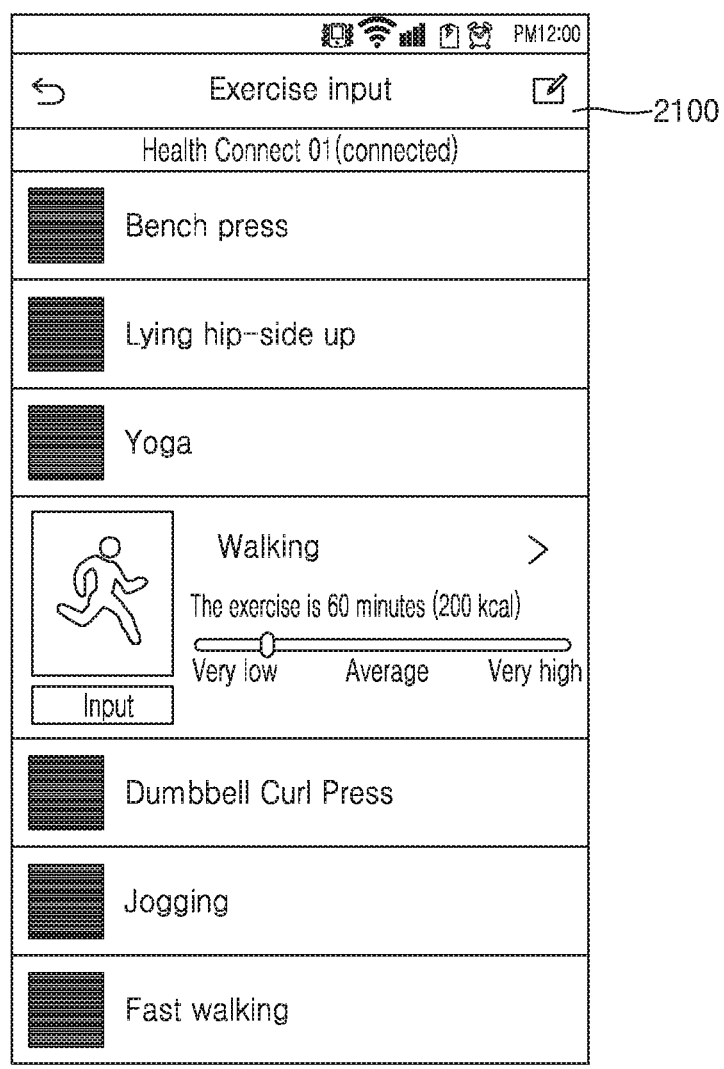

FIGS. 13 to 21 are diagrams illustrating an example of a screen of a user terminal implementing a diabetes management method according to the present disclosure. More particularly, FIGS. 13 to 16 are diagrams illustrating an example of a screen for blood sugar management, FIGS. 17 and 18 are diagrams illustrating an example of a screen for diet management, and FIGS. 19 to FIG. 21 are diagrams illustrating an example of a screen for exercise management.

Figure 13:
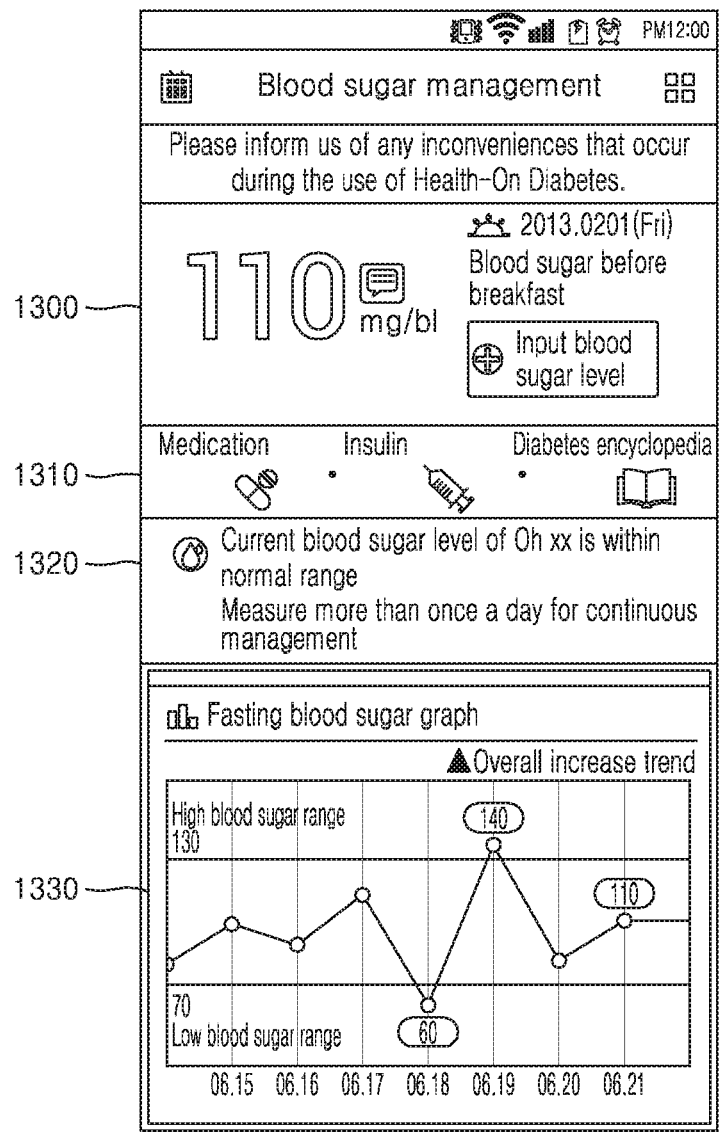
FIGS. 13 to 21 are diagrams illustrating an example of a screen of a user terminal implementing a diabetes management method, according to the present disclosure.

Referring to FIG. 13, a basic screen for blood sugar management may include a blood sugar information screen 1300 for displaying information about recent blood sugar measurement values, blood sugar measurement times, or dates, a medication information screen 1310 for displaying information about the dose of oral diabetes drugs or insulin or general diabetes knowledge, an information display screen 1320 for displaying the feedback information received from the diabetes management server, and a graph screen 1330 for providing a graph of blood sugar values for a certain time.

Figure 14:
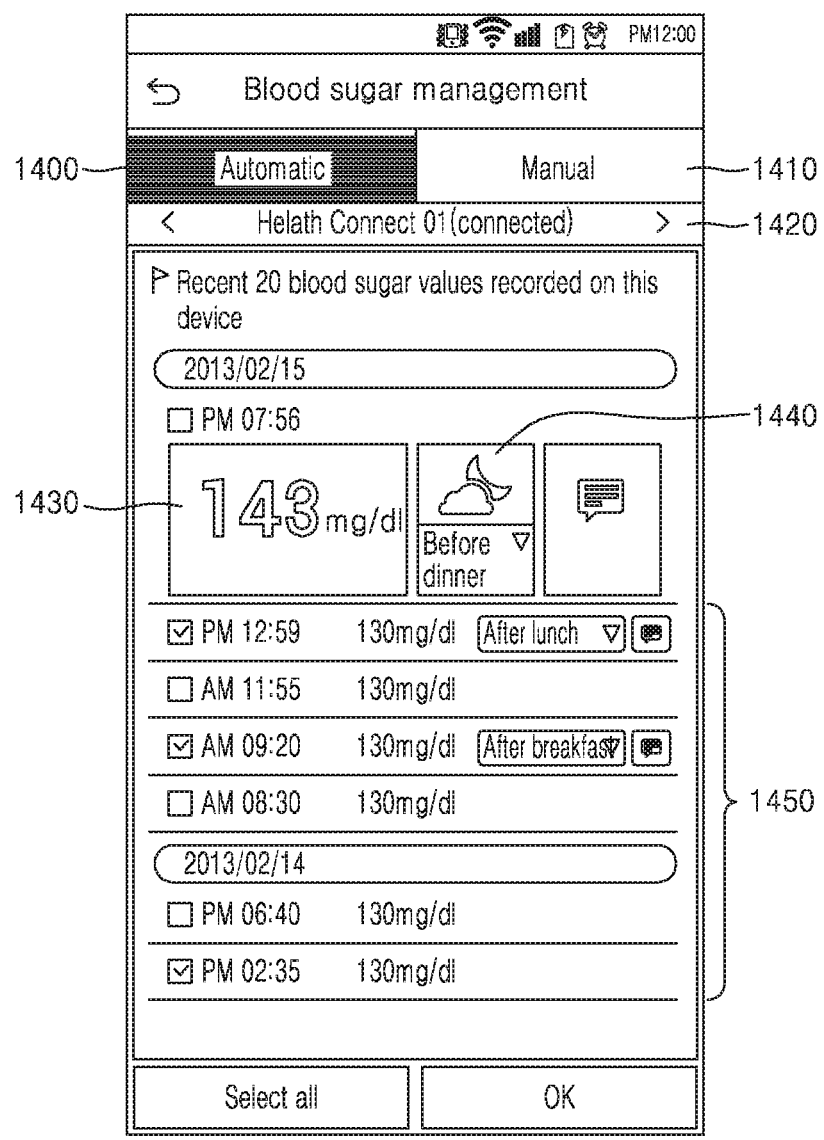

Referring to FIG. 14, the user terminal may include an automatic mode 1400 for automatically receiving a blood sugar measurement value from the blood sugar meter and a manual mode 1410 for directly receiving an input of a blood sugar measurement value from the user. FIG. 14 illustrates a case where it is connected to the blood sugar meter to automatically receive an input of the blood sugar measurement value, and a connection/disconnection state 1420 with respect to the blood sugar meter is displayed on the screen. The user terminal may display a blood sugar measurement value 1430 received from the blood sugar meter and provide a menu 1440 for selecting a blood sugar measurement time. Also, the user terminal may provide a previously-input blood sugar measurement value list 1450 to allow the user to select the previous blood sugar measurement values as well as the current blood sugar measurement value and transmit the same to the diabetes management server.

Referring to FIG. 15, the user terminal may display a screen 1500 for selecting the cause of hypoglycemia when hypoglycemia occurs. The user terminal may transmit information about the cause of hypoglycemia, which is selected from the list or is directly inputted by the user, to the diabetes management server.

Referring to FIG. 16, when the user selects a medication icon displayed on the medication information screen 1310 of FIG. 13, the medication state and history of the user may be detected from the screen.

FIGS. 17 and 18 illustrate examples of a screen for diet management, which may display information about the food calorie intake of the user. The user may easily input the food calorie intake through a diet input screen 1800.

FIGS. 19 to 21 illustrate examples of screens for exercise management, which may include a screen 1900 for displaying information such as a target calorie amount and a current calorie amount, a screen 2100 for inputting a current exercise type, and a screen 2000 for displaying the activity amount received from the activity amount meter (e.g., the number of steps in the case of walking) in association with a selected exercise type.

The present disclosure may also be embodied as computer-readable codes on a computer-readable recording medium. The computer-readable recording medium may be any data storage device that may store data that may be thereafter read by a computer system. Examples of the computer-readable recording medium may include read-only memories (ROMs), random-access memories (RAMs), compact disk read-only memories (CD-ROMs), magnetic tapes, floppy disks, and optical data storage devices. The computer-readable recording medium may also be distributed over network-coupled computer systems so that the computer-readable codes may be stored and executed in a distributed fashion.

The present disclosure has been particularly shown and described with reference to example embodiments thereof. However, those of ordinary skill in the art will understand that various changes in form and details may be made therein without departing from the spirit and scope of the present disclosure as defined by the appended claims. Therefore, the described embodiments should be considered in descriptive sense only and not for purposes of limitation. Thus, the scope of the present disclosure may be defined not by the above descriptions but by the appended claims, and all differences within the equivalent scope thereof will be construed as being included in the present disclosure.

The invention claimed is:

1. A diabetes management method based on a diabetes management server connected to a user terminal through a wired/wireless communication network, the diabetes management server including a database defining a monitoring procedure for patient groups, the diabetes management method comprising:

receiving a blood sugar measurement value from the user terminal;

detecting, from the database, a monitoring procedure for a patient group including the user;

generating feedback information about the blood sugar measurement value by using the detected monitoring procedure; and transmitting the generated feedback information to at least one of the user terminal, a carer terminal of the user, a call center, and a medical staff terminal, wherein the patient groups comprise a first patient group capable of being managed without antidiabetic drugs, a second patient group capable of being managed by oral antidiabetic drugs that do not cause hypoglycemia, a third patient group capable of being managed by oral antidiabetic drugs capable of causing hypoglycemia, and a fourth patient group capable of being managed by insulin, and the generating of the feedback information comprises, in response to determining that a blood sugar measurement value of the user belonging to the third or fourth patient group belongs to hypoglycemia, transmitting, to the user terminal, feedback information for requesting a response within a certain time, and in response to determining that there is no response within the certain time, transmitting a message to the carer terminal.

2. The diabetes management method of claim 1, wherein the receiving comprises receiving a blood sugar measurement time, and the detecting comprises detecting a monitoring procedure for a blood sugar measurement time from among the monitoring procedure for the patient group including the user.

3. The diabetes management method of claim 1,
wherein the generating of the feedback information comprises, in response to determining that the user belonging to the fourth patient group has hypoglycemia, generating feedback information including an insulin increase/decrease according to a blood sugar measurement value of the user, and in response to determining that an insulin dose according to the insulin increase/decrease is outside a predetermined range, transmitting a message to the medical staff terminal.

4. The diabetes management method of claim 1, further comprising:

receiving information about a current calorie intake from the user terminal;

detecting a body mass index of the user;

when the body mass index is equal to or greater than a first threshold value, detecting a difference between the current calorie intake and a suitable calorie intake for a diabetic patient;

when the body mass index is smaller than the first threshold value or the current calorie intake is smaller than the suitable calorie intake, providing a nutritionally balanced diet program based on the current calorie intake;

when the current calorie intake is greater than the suitable calorie intake and smaller than a second threshold value, providing a weight control program based on the suitable calorie intake; and when the current calorie intake is greater than the suitable calorie intake by the second threshold value or more, providing a weight control program based on the calorie value obtained by subtracting the second threshold value from the current calorie intake.

5. The diabetes management method of claim 1, further comprising:

when the user has a complication or belongs to an exercise risk group, providing an activity amount increase program;

when the user belongs to a first patient group capable of being managed without antidiabetic drugs or belongs to a second patient group capable of being managed by oral antidiabetic drugs that do not cause hypoglycemia, providing a physical fitness program or a weight loss program according to a body mass index; and when the user belongs to a third patient group capable of being managed by oral antidiabetic drugs capable of causing hypoglycemia or belongs to a fourth patient group capable of being managed by insulin, providing the physical fitness program.

6. A diabetes management method based on a user terminal connected to a blood sugar meter through wired or wireless communication, the user terminal including an automatic mode for receiving a blood sugar measurement value from the blood sugar meter and a manual mode for providing an interface screen for receiving an input of a blood sugar measurement value from a user, the diabetes management method comprising:

transmitting, to a diabetes management server, blood sugar measurement time information together with a blood sugar measurement value acquired through the automatic mode or the manual mode; and receiving, from the diabetes management server, and displaying feedback information generated based on the blood sugar measurement time and the blood sugar measurement value, by using a predetermined monitoring procedure for a patient group including a user, wherein the receiving and displaying of the feedback information comprises:

in response to determining that the user belongs to a patient group capable of being managed by oral antidiabetic drugs capable of causing hypoglycemia or a patient group capable of being managed by insulin, and the blood sugar measurement value corresponds to hypoglycemia, receiving and displaying feedback information for requesting a response within a certain time;

in response to determining that a user response is received within the certain time, transmitting the user response to the diabetes management server; and receiving a guide message for overcoming hypoglycemia from the diabetes management server.

7. The diabetes management method of claim 6, wherein the receiving and displaying of the feedback information comprises, when the user belongs to a patient group capable of being managed by insulin, receiving feedback information including an insulin increase/decrease according to a blood sugar measurement value of the user.

8. The diabetes management method of claim 6, further comprising:

providing to the user a screen interface for receiving an input of food intake information of the user for each time zone, and detecting information about a current calorie intake relating to the food intake information received through the screen interface; and providing, based on the current calorie intake information and a body mass index of the user, at least one of a nutritionally balanced diet program based on the current calorie intake, a weight control program based on a suitable calorie intake for a diabetic patient, and a weight control program based on the number of calories obtained by subtracting a predetermined number of calories from the current calorie intake.

9. The diabetes management method of claim 6, further comprising:

receiving an input of an activity amount from an activity amount meter connected through wired or wireless communication; and providing a physical fitness program or a weight loss program based on a body mass index of the user, the activity amount, and information about a patient group including the user, from among a patient group capable of being managed without antidiabetic drugs, a patient group capable of being managed by oral antidiabetic drugs that do not cause hypoglycemia, a patient group capable of being managed by oral antidiabetic drugs capable of causing hypoglycemia, and a patient group capable of being managed by insulin.

* * * * *